United States Patent

Fortuin et al.

[11] Patent Number: 6,127,501
[45] Date of Patent: Oct. 3, 2000

[54] POLYETHYLENE MEMBRANE STEAM-STERILIZABLE AT 134° C.

[75] Inventors: Henricus M. Fortuin, Maastricht; Petrus H. M. Stokman, Geleen, both of Netherlands

[73] Assignee: DSM N.V., Heerlen, Netherlands

[21] Appl. No.: 07/975,074

[22] Filed: Nov. 12, 1992

[30] Foreign Application Priority Data

Nov. 11, 1991 [NL] Netherlands ............................ 9101876

[51] Int. Cl.$^7$ ................................................. C08F 110/02
[52] U.S. Cl. .................................. 526/348.1; 210/500.36; 428/220; 428/910; 521/143; 528/502 B; 528/503
[58] Field of Search ................... 526/348.1; 210/500.36; 528/503, 502 B; 264/235.6, 235.8; 428/220, 98, 910

[56] References Cited

U.S. PATENT DOCUMENTS

| | | | |
|---|---|---|---|
| 3,351,495 | 11/1967 | Larsen et al. | 210/500.36 |
| 3,558,764 | 1/1971 | Isaacson et al. | 264/235.6 |
| 3,801,692 | 4/1974 | Zimmerman | 264/235.6 |
| 3,839,516 | 10/1974 | Williams et al. | 264/41 |
| 4,113,935 | 9/1978 | Schippers et al. | 526/348.1 |
| 4,311,660 | 1/1982 | Barham et al. | 528/503 |
| 4,384,023 | 5/1983 | Okamura et al. | 428/523 |
| 4,545,950 | 10/1985 | Motooka et al. | 526/348.1 |
| 4,600,633 | 7/1986 | Kono et al. | 526/348.1 |
| 4,612,148 | 9/1986 | Motooka et al. | 264/49 |
| 4,620,955 | 11/1986 | Kono et al. | 264/41 |
| 4,620,956 | 11/1986 | Hamer | 264/235.6 |
| 4,743,375 | 5/1988 | Seita et al. | 428/523 |
| 4,778,601 | 10/1988 | Lopatin et al. | 210/500.36 |
| 4,873,034 | 10/1989 | Kono et al. | 210/500.36 |
| 4,900,444 | 2/1990 | Seita et al. | 210/500.36 |
| 4,927,576 | 5/1990 | Seita et al. | 264/49 |
| 4,948,544 | 8/1990 | Van Unen et al. | 264/235.8 |
| 5,152,946 | 10/1992 | Gillette | 264/235.8 |
| 5,238,618 | 8/1993 | Kinzer | 264/235.6 |
| 5,248,461 | 9/1993 | Pluyter et al. | 264/41 |
| 5,258,156 | 11/1993 | Kurauchi et al. | 264/235.6 |
| 5,370,889 | 12/1994 | Fortuin et al. | 526/348.1 |
| 5,376,445 | 12/1994 | Fortuin et al. | 526/348.1 |
| 5,411,695 | 5/1995 | Yamada et al. | 264/235.6 |
| 5,430,119 | 7/1995 | Kouya et al. | 526/348.1 |

FOREIGN PATENT DOCUMENTS

| | | |
|---|---|---|
| 342026 | 11/1989 | European Pat. Off. . |
| 1207611 | 12/1965 | Germany ............................ 264/235.5 |
| 56-159587 | 3/1981 | Japan . |
| 62-6451101 | 8/1987 | Japan . |
| 380294 | 8/1989 | Japan . |
| 1684293 | 12/1988 | U.S.S.R. . |
| 1051320 | 12/1966 | United Kingdom . |

*Primary Examiner*—Fred Teskin
*Attorney, Agent, or Firm*—Pillsbury Madison & Sutro LLP

[57] ABSTRACT

Porous polyolefin membrane with a porosity of at least 20%, which is steam sterilizable at elevated temperature, wherein the polyolefin is polyethylene with an intrinsic viscosity of at least 5 dl/g and the membrane shows a shrinkage of at most 4% in every direction in the plane of the membrane when exposed to steam with a temperature of 134° C. for 10 minutes.

17 Claims, No Drawings

POLYETHYLENE MEMBRANE STEAM-STERILIZABLE AT 134° C.

The invention relates to a process for making a porous polyolefin film steam-sterilizable by subjecting the porous film at elevated temperature to a heat treatment.

Such a process is known from EP-A-217.698, in which a non-stretched porous polyolefin film obtained by melt extrusion is subjected to a heat treatment, which comprises the exposure of the film to a temperature which is 20–50° C. below the melting point of the polyolefin and at which the dimensions of the film are kept constant. The film so treated has been found to be capable of being sterilized with steam with a temperature of 121° C. and during this sterilization to show a linear shrinkage of 6% at most. An essential condition mentioned on page 5, lines 51–56, of said patent application is that during the entire process of producing and heat treating the film any form of stretching of the film should be avoided.

The disadvantage of this process is that no porous steam-sterilizable membranes can be produced with it from stretched porous films, while stretching is a very frequently used process step in the production of very thin and highly porous films, which exactly are particularly suited for membrane applications.

The object of the invention is to provide a process for producing a steam-sterilizable porous membrane starting from a stretched porous polyolefin film.

This object is achieved according to the invention in that a porous film, which has been produced from a solution of the polyolefin and stretched into at least one direction, is subjected to a heat treatment comprising a shrink treatment in which the film is exposed, in a gaseous atmosphere, to a temperature which at least equals the temperature at which during use of the treated film the steam sterilization will be conducted and which does not exceed the melting temperature of the polyethylene and in which treatment shrinkage is allowed to take place in every direction in the plane of the film, which shrinkage amounts to at least 95% of the critical shrink factor in the relevant direction at the temperature at which the steam sterilization will be conducted.

The membrane obtained by applying this process has been found to show in steam sterilization at a temperature which is equal to or lower than the temperature at which the heat treatment is conducted a shrinkage of 3.5% at most, and in many cases even 2.5% at most, in every direction of the plane of the film. A membrane having this property will hereinafter be referred to as a steam-sterilizable membrane.

A further surprising advantage of the process according to the invention is that despite the shrink treatment the resulting membrane has been found to show virtually the same porosity and air permeability as the original stretched porous film.

The critical shrink factor at a chosen temperature in a certain direction of a film is defined as $$\frac{l_0 - l_1}{l_0} \times 100\%$$

In this formula $l_0$ is the linear dimension of the film in that direction, before shrinking, and $l_1$ is the residual length in that direction after exposure of the film to said temperature for 20 minutes in a gaseous atmosphere, wherein the film is allowed to shrink freely.

Steam sterilization is according to standard procedures usually carried out using steam of about 2 and 3 bar for 0.5–2 hours or for 5–10 minutes respectively. The temperature at which during use of the membrane the steam sterilization will be conducted therefor usually is 121 or 134° C., the temperature of 2 or 3 bar steam respecting. The second method is preferred for economic reasons on account of the much shorter duration. That is why the invention is especially directed to a process wherein the temperature at which the shrink treatment is carried out, hereinafter to be referred to as the shrinking temperature, and at which the membrane can be subjected to steam sterilization without impermissible shrinkage is preferably at least 134° C. A membrane thus produced is even resistant to such conditions as prevail during the cleaning of installations using steam under a pressure of about 3 bar, so that such cleaning can be effected without the membrane having to be removed and having to be put back. Steam with a temperature of 134° C. has a pressure of about 3.2 bar, so that by using such steam the cleaning of the installation and the sterilization of the membranes contained therein can be effected in one and the same step. Under the said conditions, the shrinkage that occurs in the membrane produced by applying the process according to the invention is only 4% at most. In a membrane with a higher degree of shrinkage in one or more directions in the plane of the membrane, tensions induced in the membrane may be too high, in consequence of which the pore structure may be adversely affected and the membrane properties can be influenced unfavourably, or under which tensions the membrane could even collapse.

A further advantage of the process according to the invention is that it is suited also for producing membranes, steam-sterilizable at 134° C., of polyethylene having a high intrinsic viscosity of, for instance, at least 5 dl/g, determined in decalin at 135° C. This cannot be achieved with the process according to the state of the art, because in that process the heat treatment can only be carried out at a temperature not higher than 20° C. below the melting point, that is at about 120° C. In a steam sterilization process at 134° C., a film treated in that way will show an impermissibly high degree of shrinkage. A membrane produced from polyethylene with an intrinsic viscosity of at least 5 and preferably of at least 6 dl/g, measured in decalin at 135° C., has favourable mechanical properties, particularly a favourable combination, as far as membranes go, of tensile strength and elongation at break. The process according to the invention is therefore preferably applied to polyethylene with an intrinsic viscosity of at least 5 and preferably at least 6 dl/g.

Processes for producing stretched porous polyolefin films are known per se, for instance from EP-A-193.318. Processes particularly suited for producing polyethylene films from solutions of polyethylene having the said intrinsic viscosity are known in the art, for instance from EP-A-378.279. According to the process disclosed in the latter publication, films with porosities of up to 90% can be produced from polyethylene having an intrinsic viscosity of at least 5 dl/g by stretching into at least one direction at elevated temperature, but below the melting point of the polyethylene of films formed from a polyethylene solution. These stretched films show a very high degree of shrinkage at elevated temperature and can therefore not as such be used as sterilizable membrane. However, such films have been found to be highly suited for use in the process according to the invention for the production of a steam-sterilizable membrane. The thickness with which porous stretched polyethylene films can be produced by applying said process may vary within wide limits. Preference is given to the use of porous films having a thickness of between 2 and 500 μm, from which, by applying the process according to the invention, membranes can be obtained having a thickness of 5–1000 μm. In this connection it should be noted that during the shrinking in the plane of the film, in which process the area thereof decreases, the thickness of the film usually increases.

A membrane within the said range of thickness, having a porosity of at least 20%, can on the one side conform to the requirement imposed on membranes that it should preferably be self-supporting and resistant to a certain pressure differential over the membrane and on the other side to the requirement that through the membrane an adequate gas or water flux should be possible. In order to obtain a maximum flux, the porosity of the membrane is preferably at least 50% and more preferably at least 65%.

The shrinking of the film at elevated temperature takes place by exposing it to a shrinking temperature which at least equals the sterilization temperature to be applied during use of the membrane. Such exposure takes place in a gaseous atmosphere, for instance in air, steam, under nitrogen or another inert gas, which has the advantage that the usual ovens can be used. If the film is exposed to a shrinking temperature higher than the melting temperature of the polyethylene, the film will melt and lose its porosity and form, so that the shrinking must be effected below the melting point of the polyolefin.

The shrinkage admitted in every direction in the plane of the film must be at least 95% of the critical shrink factor in that direction and at the sterilization temperature. The easiest, and therefore preferred, manner of admitting shrinkage in all directions is by allowing the film to shrink into two mutually perpendicular directions in the plane of the film. The critical shrink factor strongly depends on the history of the film and must be determined by experiment. This critical shrink factor generally increases as the film is stretched further and more rapidly, but during steam sterilization the film may shrink also into a direction into which no stretching may have taken place. A difference has been found often to occur also in the shrinkage of an extruded film into the extrusion direction (generally referred to as Machine Direction, MD) and into the direction perpendicular thereto (Transverse Direction, TD). It has been found also to make a difference if in biaxial stretching, that is stretching into two directions that are generally perpendicular to each other, the stretching into the two directions has taken place simultaneously or sequentially, so first into one and then into the other direction. Now, by determining the critical shrink factor in one direction of stretch and in the direction perpendicular thereto and by admitting, in the two directions, a possibly different degree of shrinkage, calculated by means of the relevant critical shrink factor, a membrane is obtained having virtually the same properties in all directions. The critical shrink factor as calculated according to the definition given hereinbefore is representative as long as the conditions under which the stretched films are produced are not changed, so that the shrink factors calculated on a sample of the stretched film are valid also for other films produced under the same conditions. The stretched porous film must be shrunk to at least 95% of the critical shrink factor. Such shrinkage has been found generally to suffice for obtaining a membrane that does not shrink more than 4% in all directions when exposed to the sterilization temperature. Preference, however, is given to an admitted shrinkage to the full critical shrink factor, because the membranes then obtained have been found at the sterilization temperature to show virtually no shrinkage at all any more.

The stretched film must be shrunk at a temperature at least equalling the sterilization temperature. It is an advantage for the chosen shrinkage temperature to be a few degrees, for instance 1–3° C., higher than the sterilization temperature and for the film also to be shrunk to the critical shrink factors that go with such higher shrinking temperature. This will raise the temperature at which the membrane is still steam sterilizable to rise, which provides a safety margin against temperature deviations that might occur during the sterilization process.

In the shrinking process, it must be possible for the dimensions of the film to be fixed at the final dimensions based on the critical shrink factor in every direction. The dimensions of the stretched film before the shrinking are considerably larger than the said final dimensions and the device used for the fixing must also be capable, during the shrinking process, of following the reduction of the size of the film. These requirements can be met by using devices known per se. For instance, in the usual biaxial stretching lines known in the art a second unit analogous to the stretching device can be incorporated in which the stretching elements move into a direction opposite to that of the stretching section, thus permitting a controlled reduction of the film surface. In the process, shrinkage is then, for instance, admitted into the longitudinal direction of the film by choosing for the shrunk film, in the desired ratio, a winding speed lower than the speed at which the stretched film is supplied to the second unit. If the stretching is done on a stretching frame, the shrinking can be carried out immediately after the stretching by allowing the surface of the stretched film, after having reached the required shrinking temperature, and as the film is still clamped in the stretching frame, to be reduced at the desired speed to its final dimensions.

The speed at which the film is allowed to shrink may vary between wide limits. It is possible for the film to be constantly kept under a low tension and for the dimensions of the tensioned film to be gradually reduced as the shrinkage continues. Also, by setting the motions of the shrinking device it is possible for the expected shrinkage to be anticipated, so that the film is not tightly stretched, but in that case care must be taken that the film which, at the elevated shrinking temperature, is apt to get deformed and will sag under its own weight and fold easily, too, does not come into contact with parts of the stretching device or get stuck in possible folds of its own. An almost maximum shrinking speed at which the above problems are avoided is obtained when the film is allowed to shrink virtually free from tension by causing the motions of the shrinking device to follow the reduction of the dimensions as far as possible.

Surprisingly, the porosity of the shrunk film is virtually the same as that of the original stretched film. This is all the more surprising in this case, because the stretched film, which had only a very low porosity before the stretching, acquired its porosity actually by the process opposite to shrinking at elevated temperature, viz. stretching at elevated temperature and that at a temperature even lower than that at which the shrinkage takes place. An additional advantage of the process according to the invention is an economically highly acceptable yield of the desired membrane, because the surface area of the re-shrunk membrane, though, as a result of the admitted shrinkage, smaller of course than that of the original stretched film, is considerably larger, up to even 20 times, than the original film before the stretching.

The membrane produced by applying the process according to the invention can be used to advantage in, for instance, sterilizable clothing and for covering wounds in the medical sector and as separating filter in the pharmaceutical and food industries.

Porous membranes of polyethylene with an intrinsic viscosity of at least 5 dl/g, which membranes are steam-sterilizable at 134° C., have not been known so far, nor has it been possible, as indicated hereinbefore, for them to be produced by applying the process according to the state of the art, or to be derived herefrom. The invention therefore also relates to a porous polyolefin membrane with a porosity of at least 20%, steam-sterilizable at a temperature of at least 121° C., characterized in that the polyolefin is polyethylene with an intrinsic viscosity of at least 5 dl/g and that on exposure to steam with a temperature of 134° C. for 10 minutes the membrane shrinks by 4% at most in every direction in the plane of the membrane. The membrane preferably shrinks 2.5% at most. The porosity is preferably at least 50% and more preferably at least 65%.

The invention will be elucidated by means of the following examples without, however, being limited thereto. The parameters mentioned are determined in the manner described below, or previously described above.

The intrinsic viscosity of the polyethylene is determined in decalin at 135° C.

The thickness of the films is measured with a Millitron Feinpruff meter, whose tracer has a curvature radius of 12 mm.

The cross flow waterflux is determined by causing water at room temperature to flow along the surface of a clamped sample of the membrane, the pressure on the side where the water flows being 2 bar higher than the pressure on the other side. The waterflux is now calculated on the basis of the amount of water in 1 H$_2$O/h.bar.m$^2$ pressed under these conditions through the membrane.

The air permeability, standardized at a thickness of 100 um of the membrane, is determined in s/50 ml.100 um based on the Gurley value according to ASTM standard D726-58 with a measuring area of 6.45 cm$^2$ (1 sq. inch) under a weight of 567 kg.

The density of the film is determined on the basis of the weight and the volume of a piece of film cut from the film or from the membrane.

The porosity is determined on the basis of the measured density ρ of the porous film or of the porous membrane and the density of the polyethylene bulk material $\rho_0$ as:

$$\text{porosity} = \frac{\rho_0 - \rho}{\rho_0} \times 100\%$$

EXAMPLE I

A 20% (wt) solution of polyethylene with a melting point of about 140° C. and an intrinsic viscosity of 15.5 dl/g in decalin, corresponding with a weight-average molecular weight of 2.2×10$^6$ g/mole, is extruded at a temperature of 180° C. The extruder head is provided with a slot die measuring 400×1 mm. The extruded film is passed into a cooling bath containing water with a temperature of 20° C. The gel film thus obtained is stripped of solvent by evaporation in an oven at a temperature of 70° C., in which process the length of the film is kept constant. A piece of film measuring 85 mm×85 mm, cut from the film after stripping of the solvent, is placed in an Iwamoto stretching frame and stretched 5×into successively two directions at 130° C.

After cooling the stretched film in the stretching frame, a sample measuring 10 cm×10 cm is cut from the film and placed in an air-heated oven at 135° C. for 10 minutes allowing the film to shrink freely. After cooling to room temperature, the dimensions of the shrunk film are 67×53 cm. The critical shrink factors in both directions of stretch are calculated on this basis and amount to 33 and 47% respectively. Also, on samples of the stretched film the porosity, the air permeability and the cross flow waterflux are determined. A second piece measuring 85 mm×85 mm is stretched under the above-mentioned conditions. The film is then brought to 135° C. and the dimensions of the stretching frame are set to the dimensions of the film after shrinking to 90% of the critical shrink factors. This at first causes the film to hang slack in the stretching frame, but soon the film tightens in consequence of the shrinkage. When the film is tight, the dimensions of the stretching frame are set at the calculated dimensions of the film after shrinking to the full critical shrink factors. After that the film tightens again. The shrunk film is cooled and is found, after removal of the stretching frame, to be completely flat. On samples from the shrunk film the following parameters are determined: the shrinkage on exposure to steam with a temperature of 135° C. for 10 minutes, the porosity, the air permeability and the cross flow waterflux. The values of these parameters before and after the shrinking are shown in Table 1.

TABLE 1

|  | Before shrinking | After shrinking |
|---|---|---|
| Thickness (μm) | 60 | 116 |
| Porosity (%) | 80 | 74.7 |
| Air permeability (sec/50 ml · 100 μm) | 17.4 | 24.3 |
| Cross flow waterflux (1 H$_2$O/h · bar · m$^2$) | 200 | 270 |
| Critical shrink factor at 135° C. (MD % × TD %) |  | 33 × 47 |
| Shrinkage in steam of 135° C. (MD % × TD %) |  | 0 × 0 |

EXAMPLE II

Example I is repeated except that during the shrink treatment shrinkage is permitted to 95% of the critical shrink factors. The thickness of the shrunk film is 73 μm and the shrinkage in steam of 135° C. (MD×TD) 2%×2.3%. The air permeability before and after the shrinking is 8 and 10.1 sec/50 ml.100 μm respectively.

COMPARATIVE EXPERIMENT A

Example II is repeated except that shrinkage is permitted to 90% of the critical shrink factors. The thickness of the shrunk film is 85 μm and the shrinkage in steam of 135° C. (MD×TD) 6%×5%, so more than 4%×4%. Consequently, the re-shrinking of the stretched film to less than 95% of the critical shrink factor does not yield a steam-sterilizable membrane.

COMPARATIVE EXPERIMENT B

Example I is repeated except that a film stretched 5×5 times is re-shrunk to the critical shrink factors determined at 125° C. During steam sterilization at 135° C. the film thus shrunk shows a shrinkage (MD×TD) of 7%×10%. So re-shrinking at a temperature lower than the sterilization temperature does not yield a steam-sterilizable membrane.

COMPARATIVE EXPERIMENT C

Example I is repeated except that the film is sequentially stretched 6×6 times at 120° C. The critical shrink factors at 121° C. (MD×TD) are 10%×23% and at 135° C. 15%×50%. A sample of the film is shrunk at 135° C., but the shrinkage is permitted to only the critical shrink factors at 121° C.

During steam sterilization at 121° C. the shrinkage (MD× TD) is 0%×0%, at 135° C. 4%×10%. This shows that no steam-sterilizable membrane is obtained if only the condition of effecting the shrinkage at the sterilization temperature is complied with and not the condition regarding the critical shrink factors.

EXAMPLE III

A 20% (wt) solution of polyethylene with an intrinsic viscosity of 15.5 dl/g, corresponding with a molecular weight of about $2.2 \times 10^6$ g/mole, in decalin is extruded at a temperature of 180° C. The extruder head is provided with a slot die measuring 400 mm×1 mm. The extruded film is passed into a cooling bath of which the liquid surface is about 1 mm below the exit of the extrusion slot. The cooling bath contains water of 20° C. with a 3 to 4 mm thick layer of decalin so applied thereon that both sides of the film are in contact with the decalin when the film is passed into the cooling bath. From the gel film thus obtained the solvent is evaporated in an oven at a temperature of 70° C., in which process a constant film length is maintained. From this point onwards example I is repeated, except that sequential stretching of 8×8 times is applied. The critical shrink factors in the two directions of stretch are 21 and 55%. The properties of the film before and after the shrink treatment are shown in Table 2.

TABLE 2

|  | Before shrinking | After shrinking |
| --- | --- | --- |
| Thickness ($\mu$m) | 30 | 98 |
| Porosity (%) | 83.5 | 78.5 |
| Air permeability (sec/50 ml · 100 $\mu$m) | 1.7 | 2.4 |
| Cross flow waterflux (1 $H_2O$/h · bar · $m^2$) | 280 | 380 |
| Critical shrink factor at 135° C. (MD % × TD %) |  | 21 × 55 |
| Shrinkage in steam of 135° C. (MD % × TD %) |  | 0 × 0 |

EXAMPLE IV

A porous film of polyethylene with an intrinsic viscosity of 15.5 dl/g and measuring 40 cm×40 cm×46 $\mu$m, obtained by stretching in a sequential stretching line, is placed in the Iwamoto stretching frame and shrunk, as described in Example I, at 135° C. The critical shrink factors are 15% and 22% respectively. The data of the film before and after the shrinking are shown in Table 3.

TABLE 3

|  | Before shrinking | After shrinking |
| --- | --- | --- |
| Thickness ($\mu$m) | 46 | 70 |
| Porosity (%) | 84 | 80 |
| Air permeability (sec/50 ml · 100 $\mu$m) | 3.3 | 7.7 |
| Cross flow waterflux (1 $H_2O$/h · bar · $m^2$) | 300 | 410 |
| Critical shrink factor at 135° C. (MD % × TD %) |  | 15 × 22 |
| Shrinkage in steam of 135° C. (MD % × TD %) |  | 0 × 0 |

EXAMPLE V

Example I is repeated, except that the intrinsic viscosity of the polyethylene is 8.4 dl/g and that the film is subjected to sequential stretching 4×4 times. The melting point of this polyethylene is about 139° C. The critical shrink factors are 15% and 27% respectively. The data of the film before and after the shrinking are shown in Table 4.

TABLE 4

|  | Before shrinking | After shrinking |
| --- | --- | --- |
| Thickness ($\mu$m) | 105 | 90 |
| Porosity (%) | 88 | 59 |
| Air permeability (sec/50 ml · 100 $\mu$m) | 10 | 32 |
| Cross flow waterflux (1 $H_2O$/h · bar · $m^2$) | 205 | 200 |
| Critical shrink factor at 135° C. (MD % × TD %) |  | 15 × 27 |
| Shrinkage in steam at 135° C. (MD % × TD %) |  | 0 × 0 |

COMPARATIVE EXPERIMENT E

Example I is repeated, except that the porous stretched film is produced from polyethylene with an intrinsic viscosity of 4 dl/g and is subjected to sequential stretching, 6×6 times. The melting point is about 138° C. The properties of the film before and after shrinking are shown in Table 5.

TABLE 5

|  | Before shrinking | After shrinking |
| --- | --- | --- |
| Thickness ($\mu$m) | 40 | 32 |
| Porosity (%) | 79 | 46 |
| Air permeability (sec/50 ml · 100 $\mu$m) | 6.8 | 0 |
| Crossflow waterflux (1 $H_2O$/h · bar · $m^2$) | 300 | 0 |
| Critical shrink factor at 135° C. (MD % × TD %) |  | 28 × 41 |
| Shrinkage in steam of 135° C. (MD % × TD %) |  | 0 × 0 |

Although the shrunk film is steam-sterilizable, and the porosity, too, is partly retained, the film from polyethylene with an intrinsic viscosity lower than 5 dl/g has been found after shrinking to have become impermeable to both air and water, so that the shrunk film is not a porous membrane.

What is claimed is:

1. A stretched porous polyethylene membrane with a porosity of at least 20% and an intrinsic viscosity of at least 5 dl/g, wherein said stretched porous polyethylene membrane has been shrunk to at least 95% of its critical shrink factor, which membrane is steam-sterilizable at elevated temperature, and displays additional shrinkage of at most 4% in every direction in a plane of the membrane when exposed to steam with a temperature of 134° C. for 10 minutes.

2. A stretched porous membrane according to claim 1, wherein the membrane shows a shrinkage of 2.5% at most.

3. A stretched porous membrane according to claim 1, wherein the porosity is at least 50%.

4. A stretched porous membrane according to claim 3, wherein the porosity is at least 65%.

5. A porous polyethylene membrane according to claim 1 wherein said membrane is 5 $\mu$m to 1,000 $\mu$m in thickness.

6. A stretched porous membrane according to claim 1, wherein said stretched porous membrane is 116 $\mu$m thick.

7. A stretched porous membrane according to claim 1, wherein said membrane is 98 $\mu$m thick.

8. A stretched porous membrane according to claim 1, wherein said stretched porous membrane is 70 or 73 $\mu$m thick.

9. A stretched porous polyethylene membrane according to claim 1, wherein the critical shrink factor is $(l_0-l_1)/l_0 \times 100\%$, wherein, $l_0$ is the linear dimension of the membrane in said relevant direction before shrinking, and $l_1$ is the residual length of the membrane, in said relevant direction after shrinking.

10. A stretched porous polyethylene membrane, wherein said stretched porous polyethylene membrane has been shrunk to at least 95% of its critical shrink factor, and is 5 to 1000 μm thick, has a porosity of at least 50%, has an intrinsic viscosity of at least 5 dl/g, is steam sterilizable at elevated temperature and on exposure to steam with a temperature of 134° C. for 10 minutes, the shrunk porous polyethylene membrane shows additional shrinkage of at most 4% in every direction in a plane of the membrane.

11. A stretched porous polyethylene membrane, wherein said stretched porous polyethylene membrane has been shrunk to at least 95% of its critical shrink factor, wherein the shrunk porous polyethylene membrane has a porosity of at least 20%, an intrinsic viscosity of at least 5 dl/g, is steam-sterilizable at elevated temperature, and said shrunk porous polyethylene membrane displays a shrinkage of at most 4% in every direction in a plane of the membrane on exposure to steam having a temperature of 134° C. for 10 minutes, wherein said membrane is obtained by producing a porous polyethylene film from a solution of polyethylene, stretching the porous polyethylene film in at least one direction, subjecting the stretched polyethylene film to a heat treatment which comprises a shrink treatment in which the stretched polyethylene film is exposed, in a gaseous atmosphere, to a temperature of at least 134° C. but which does not exceed the melting temperature of the polyethylene, wherein said heat treatment shrinkage is allowed to take place in every direction in the plane of the porous polyethylene film, wherein the shrinkage amounts to at least 95% of a critical shrink factor in the relevant direction at the temperature in which the steam sterilization will be conducted, wherein said critical shrink factor is $(l_0-l_1)/l_0 \times 100\%$, in which $l_0$ is the linear dimension of the film in said relevant direction before shrinking, and $l_1$ is the residual length in said relevant direction after exposing the film at the temperature in said gaseous atmosphere.

12. A steam sterilizable porous membrane according to claim 11, wherein said membrane is 5 to 1000 μm thick.

13. A steam sterilizable porous membrane according to claim 11, wherein said polyethylene has an intrinsic viscosity of at least 6 dl/g.

14. A steam sterilizable porous membrane according to claim 12, wherein said polyethylene has an intrinsic viscosity of at least 6 dl/g and said stretched porous membrane is 5 to 1000 μm thick.

15. A steam sterilizable porous membrane according to claim 11, wherein the porosity is at least 50%.

16. A steam sterilizable porous membrane according to claim 15, wherein the porosity is at least 65%.

17. A stretched porous polyethylene membrane according to claim 10, wherein the critical shrink factor is $(l_0-l_1)/l_0 \times 100\%$, wherein, $l_0$ is the linear dimension of the membrane in said relevant direction before shrinking, and $l_1$ is the residual length of the membrane, in said relevant direction after shrinking.

* * * * *